United States Patent [19]

Oliva

[11] Patent Number: 5,040,981
[45] Date of Patent: Aug. 20, 1991

[54] DENTAL RESTORATION HOLDER AND PLACEMENT TOOL

[76] Inventor: William E. Oliva, 18112 Carolyn Cir., Villa Park, Calif. 92667

[21] Appl. No.: 301,224

[22] Filed: Jan. 24, 1989

[51] Int. Cl.⁵ .............................................. A61C 3/00
[52] U.S. Cl. .................................... 433/141; 433/215
[58] Field of Search ...................... 433/3, 26, 141, 50, 433/215, 218; 294/1.2, 19.1; 81/7

[56] References Cited

U.S. PATENT DOCUMENTS

| | | | |
|---|---|---|---|
| 3,584,908 | 6/1971 | Ray | 294/1.2 |
| 4,073,530 | 2/1978 | Seidler | 294/19.1 |
| 4,479,672 | 10/1984 | Jermyn | 294/1.2 |
| 4,822,278 | 4/1989 | Oliva et al. | 433/141 X |
| 4,834,654 | 5/1989 | Nussbaum | 433/141 |

FOREIGN PATENT DOCUMENTS

| | | | |
|---|---|---|---|
| 2002874 | 8/1970 | Fed. Rep. of Germany | 433/141 |
| 700745 | 3/1931 | France | 433/141 |
| 3525836 | 10/1986 | Netherlands | 433/141 |

Primary Examiner—Gene Mancene
Assistant Examiner—Nicholas D. Lucchesi
Attorney, Agent, or Firm—William L. Chapin

[57] ABSTRACT

A device for manipulating dental restorations, such as thin, ceramic tooth veneer of the type used in cosmetic bonding to teeth comprises an elongated, pencil-like handle structure having a tip which is releasably attachable to a surface of a veneer, affording convenient means for manipulating the veneer, as for example when bonding the veneer to a patient's tooth. A basic embodiment of the device includes a thin, small flexible circular plate attached transversely to one end of the pencil-like structure and forming the tip of the device. The outer tranverse of the tip plate, which may be flat or concave, is coated with a tacky substance providing sufficient adherence to the surface of a ceramic veneer to permit the veneer to be picked up when the plate is gently placed in contact with the surface of the veneer. The adhesion force of the tacky substance is sufficiently small to permit the tip to be disengaged from the veneer with a slight pulling force, when desired. Another embodiment of the device employs a plastically deformable tip made of a resilient, lenticular shaped body with a generally flat, adhesive-coated lower surface. The tip is adapted to conform to the irregular biting surface of a crown or bridge. Upon placement of the crown or bridge in the mouth of the patient, the handle may at the dentist's option be pulled out of the tip, the latter remaining to serve as a bite plate or seating fixture while the restoration is being bonded to existing teeth.

4 Claims, 3 Drawing Sheets

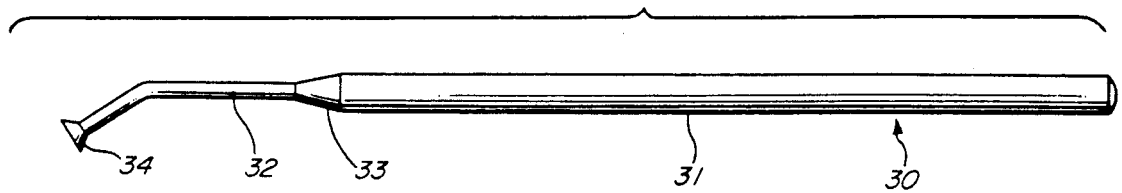
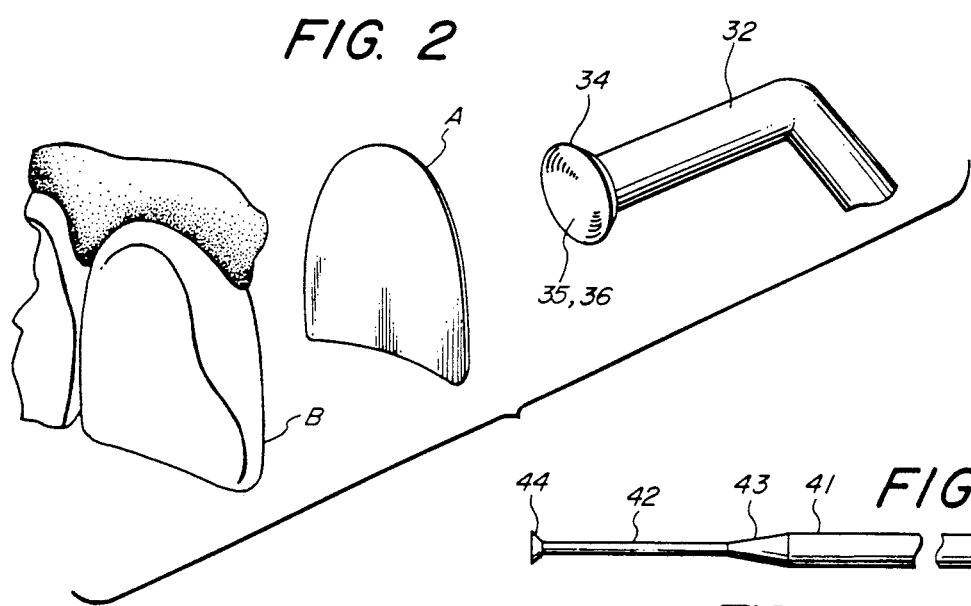
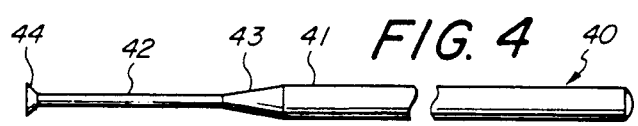
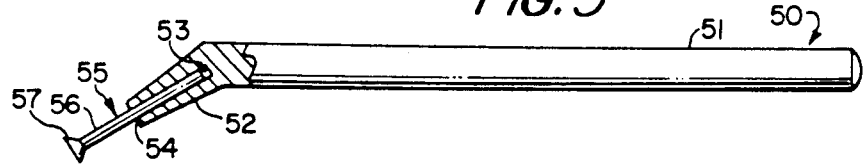
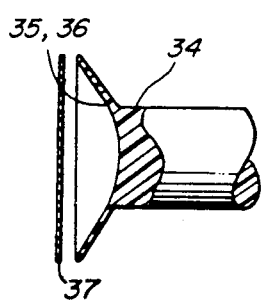
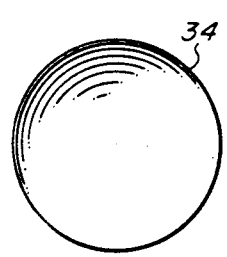
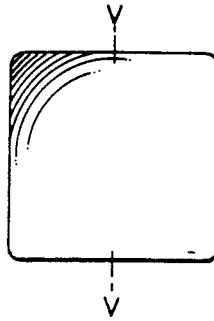
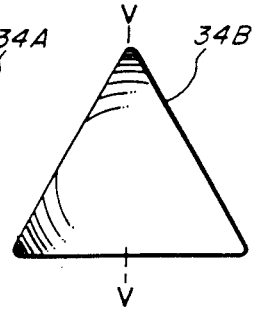

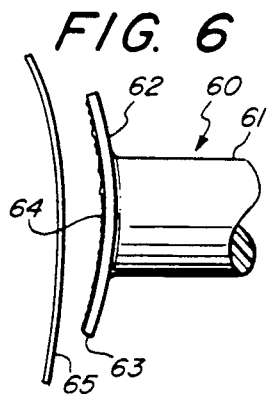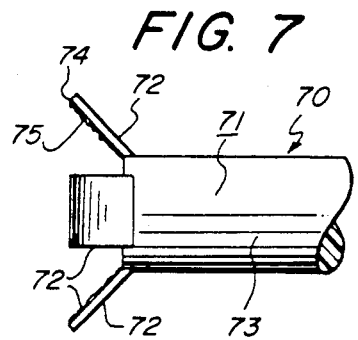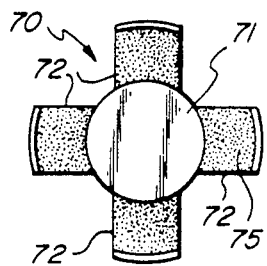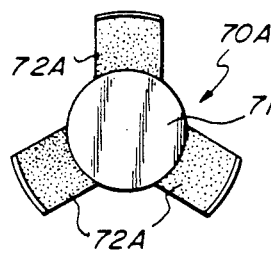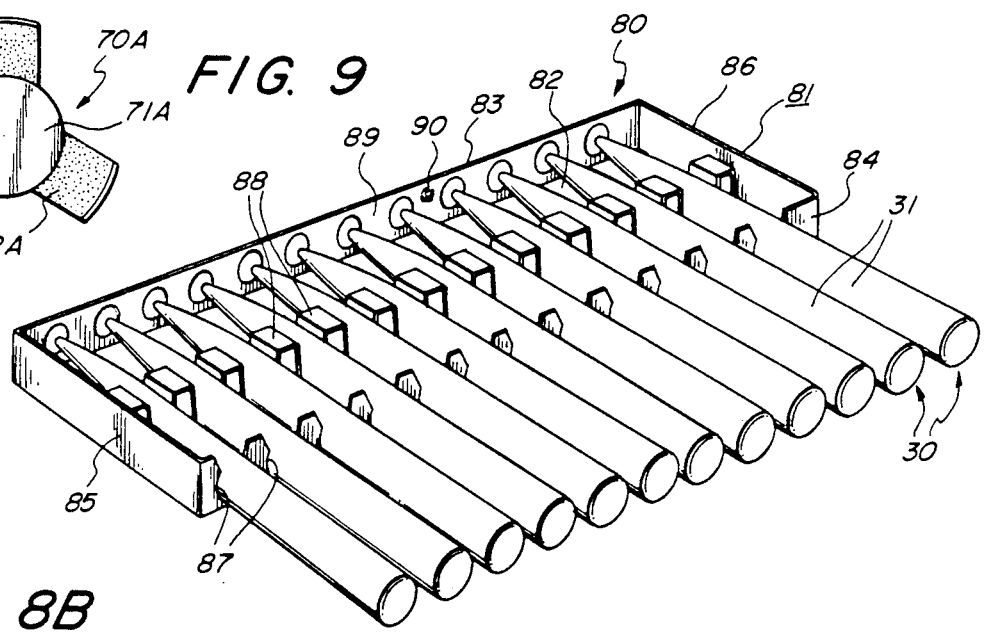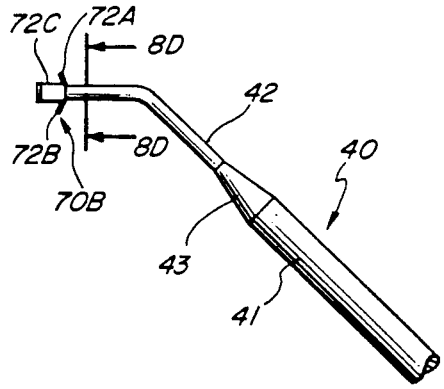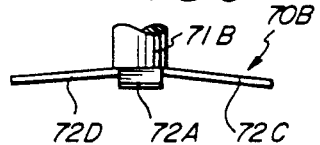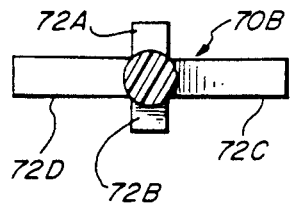

DENTAL RESTORATION HOLDER AND PLACEMENT TOOL

BACKGROUND OF THE INVENTION

1. Field of the Invention

This invention relates to instruments for use in dentistry. More particularly, the invention relates to a device for manipulating dental restorations such as thin ceramic veneers which are intended to be laminated and adhered to the outer or labial surfaces of teeth, and crowns and bridges used to cap or replace missing teeth.

2. Description of Background Art

For a variety of reasons, the enamel surfaces of teeth sometimes become permanently stained. Prolonged use of the antibiotic tetracycline, for example, can permanently discolor the teeth. The degree of discoloration of the enamelled surface of teeth can in some cases be sufficient to produce a highly unsightly effect.

The appearance of badly discolored teeth can have a detrimental effect upon the self-image of a person afflicted with this condition, and can adversely affect both business and social relations of the individual. With these factors in mind, dental health care professionals have developed a technique for treating severely discolored teeth.

In a procedure referred to as cosmetic bonding, a thin veneer of ceramic having a shape and curvature matching the outline shape and surface curvature of a discolored tooth is laminated to the tooth by cementing the veneer to the outer or labial surface of the tooth, after the tooth has been specially prepared. The veneer has a surface coloration and gloss which duplicate that of the individual's healthy teeth. Also, the veneer is sufficiently opaque to mask the stained surface of the underlying tooth. By this procedure the individual's teeth may be restored to a pleasant appearing, healthy state.

The brief description of the cosmetic bonding of ceramic veneers to teeth given above does not convey an appreciation for the complexity and delicacy of the actual veneering procedure. In a sequence of steps requiring exercise of a substantial degree of artistic craftsmanship, the dentist must prepare each tooth to receive a ceramic veneer, and make accurate impressions of the prepared teeth. Teeth impressions are made by forming a semi-liquid dental impression material over the teeth and allowing the material to harden. The impressions are then used by a highly skilled dental ceramist, or the dentist himself, to make molds in which the required ceramic veneers are eventually cast. Each cast veneer is individually fabricated and must have the precise dimensions, coloration, luster and opacity.

The number of individually demanding steps required to fabricate each ceramic tooth veneer for cosmetic bonding results in a substantial investment in time having been expended in the production of each finished veneer. Thus, the replacement value of each custom-made veneer is high. Accordingly considerable care must be exercised in handling a veneer to avoid damaging the veneer.

Since a typical veneer has a thickness range of 0.3 mm. to 4 mm., and an average thickness of about 0.5 mm., the veneer is relatively fragile until it has been cemented (laminated) to and supported by the tooth for which it was custom fabricated to laminate.

Finished ceramic veneers are attached to the teeth by means of a light sensitive adhesive. After a number of preparation steps, each of the veneers to be laminated to one or a group of teeth is temporarily fastened to the appropriate tooth. The purpose of the temporary fitting is to check size, opacity, and coloration of each of the veneers. After this preliminary fitting, each of the veneers is removed, and both veneer and tooth thoroughly cleaned of the temporary adhesive (usually glycerine) used to hold the veneer to the tooth. The outer surface of the tooth is then coated with a light-sensitive photopolymeric adhesive, and a ceramic veneer placed in position on the tooth. Usually, this placement is done by means of the dentist's fingers. Typically, an assistant then irradiates the outer surface of the ceramic veneer with a small, intense light source. Light transmitted through the ceramic veneer causes a photochemical reaction to occur in the light-sensitive adhesive, causing it to harden.

During the light-exposure process, which takes between 20 and 60 seconds, the dentist must hold the veneer in a precisely aligned position with respect to the outer surface of the tooth. If the veneer is displaced even slightly from its aligned position during the adhesive setting process, the ceramic veneer must be ground off of the tooth, and a replacement veneer fabricated.

Because of the cost and fragility of ceramic tooth veneers, and the precision with which they must be placed on a tooth in the lamination process, it would seem desirable to provide a device for holding and manipulating a ceramic veneer, especially during the placement of the veneer on a tooth during the adhesive bonding of the veneer to the tooth. Some relatively complex vacuum holding devices have been proposed for use with ceramic dental veneers. However, a need for an efficient, low-cost device for manipulating ceramic dental veneers was perceived by the present inventor, and was a motivating factor in the development of the present invention. Some versions of the present invention are also useful for installing crowns or bridges in the mouth of a patient.

OBJECTS OF THE INVENTION

An object of the present invention is to provide an implement for manipulating and positioning thin ceramic veneers of the type used for cosmetic bonding to the visible surface of teeth, and holding a veneer in proper registration with the teeth during the bonding process.

Another object of the invention is to provide a holding and manipulating device for ceramic tooth veneers which is easily attachable to, and removable from the outer surface of the veneer.

Another object of the invention is to provide a device for manipulating a ceramic tooth veneer which is easily operable with a single hand.

Another object of the invention is to provide a device for handling ceramic tooth veneers which is of a simple and inherently low-cost design.

Another object of the design is to provide a device for handling ceramic tooth veneers in which at least that portion of the device which approaches a patient's mouth is disposable.

Another object of the invention is to provide a device for holding and manipulating dental crowns and bridges.

Another object of the invention is to provide a device for seating dental castings and holding them tightly in a precise position within the mouth of a patient while an adhesive bond is formed between the tooth and casting, by means of resilient block which adheres to the casting to permit holding and transporting the casting to a desired position within the mouth, the resilient block being compressible between the teeth of the patient to hold the casting tightly in position.

Various other objects and advantages of the present invention, and its most novel features, will become apparent to those skilled in the art by perusing the accompanying specification, drawings and claims.

It is to be understood that although the invention disclosed herein is fully capable of achieving the objects and providing the advantages described, the characteristics of the invention described herein are merely illustrative of the preferred embodiment. Accordingly, I do not intend that the scope of my exclusive rights and privileges in the invention be limited to details of the embodiments described. I do intend that reasonable equivalents, adaptations and modifications of the invention described herein be included within the scope of the invention as defined by the appended claims.

BRIEF SUMMARY OF THE INVENTION

Briefly stated, the present invention comprehends an implement for manipulating a thin, ceramic tooth veneer of the type used in cosmetic bonding. The device consists of an elongated, pencil-like structure having a tip which is adapted to easily attach to or withdraw from the surface of a ceramic tooth veneer, providing a convenient means for picking up the fragile veneer, placing it in a desired position, and then disengaging the device from the veneer.

In a basic embodiment of the novel tooth veneer manipulating device according to the present invention, the tip of the device has a thin, small, flexible circular plate disposed generally transversely to the longitudinal axis of the tip. The outer transverse face of the plate, which may be either flat or concave, is coated with a tacky substance. The tacky substance provides sufficient adherence between the coated surface of the plate and the outer, convex surface of a ceramic tooth veneer, when the plate is touched gently to the veneer. This permits the veneer to be easily picked up and manipulated. However, the adhesion force of the tacky substance is sufficiently small to permit the tip to be retracted from the veneer with a slight pulling force, after the veneer has been transported and positioned as desired.

Another embodiment of the novel dental restoration holder and placement tool according to the present invention is particularly well suited to the installation of crowns and bridges in the mouth of a patient. In this embodiment, the tip of the tool has a plurality of flexible tabs coated on their outer surfaces with a tacky substance. In a preferred arrangement, four tabs extend radially outwards from a common center to form a cruciform structure. Two opposed tabs may be of greater length to facilitate their adhesive contact with the surfaces of two or more teeth of a dental restoration.

In a variation of the crown and bridge version of the dental restoration holding and placement tool according to the present invention, the tip of the tool is made of a soft rubbery material from which the handle portion of the tool may be readily withdrawn. As in the basic embodiments of the tool, an outer surface of the tip is coated with a tacky substance adapted to adhere to replacement teeth. In this variation, the adhesive coating is intended to adhere to the biting surface of the replacement teeth, the resilience of the rubbery material of which the tip is made permitting the adhesive coated surface to conform to the irregular biting surface of the tooth. After the replacement teeth comprising the crown or bridge have been manipulated into position with the tool, the handle portion may optionally be withdrawn from the tip. The patient may then bite down on the rubbery tip to hold the restoration in place while the cement used to adhere the restoration to existing teeth is curing.

BRIEF DESCRIPTION OF THE DRAWINGS

FIG. 1 is an upper plan view of one embodiment of a dental veneer manipulating tool according to the present invention which employs an adhesive tip, showing in upper edge view a typical ceramic tooth veneer of the type which the device is used to manipulate.

FIG. 2 is a front perspective view of the tool of FIG. 1, showing a ceramic veneer and a tooth to which it is to be fitted.

FIG. 3A is a side elevation view of the front tip of the tool shown in FIGS. 1 and 2, on a somewhat enlarged scale.

FIG. 3B, 3C and 3D are front end elevation views of a variety of tips of the type shown in FIG. 3A, each having a different plan-view outline shape.

FIG. 4 is a side elevation view of a second embodiment of a dental veneer manipulating tool according to the present invention.

FIG. 5 is a side elevation view, partially in section, of a modified version of the tool shown in FIG. 4.

FIG. 6 is a side elevation view of a second type of front tip for use on the tool of FIGS. 1 and 2, on a somewhat enlarged scale.

FIG. 7 is a side elevation view of a third type of front tip for use on the tool of FIGS. 1 and 2, on a somewhat enlarged scale.

FIG. 8 is a front end elevation view of the tip of FIG. 7.

FIG. 8A is a front-end elevation view of a modification of the tip shown in FIG. 8.

FIG. 8B is a side elevation view of another embodiment of the tool according to the present invention.

FIG. 8C is a side elevation view of the tip of the tool shown in FIG. 8B.

FIG. 8D is a front-end elevation view of the tip of the tool shown in FIG. 8B.

FIG. 9 is a perspective view of a container for storing a quantity of tools of the type shown in FIGS. 1 and 2.

DETAILED DESCRIPTION OF THE INVENTION

Figure 10:
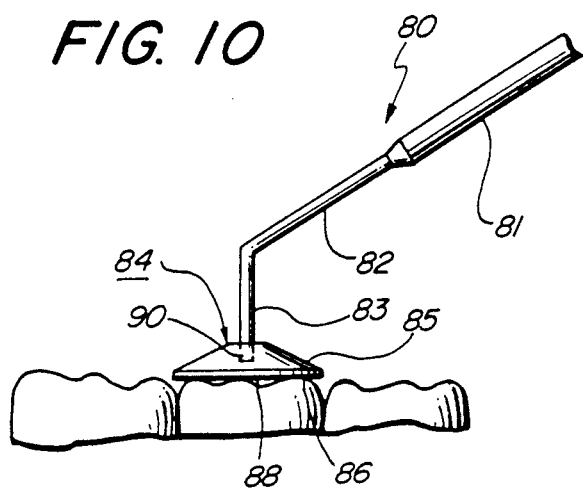
FIG. 10 is a front elevation view of a third embodiment of a dental veneer manipulating tool according to the present invention which is adapted to installing dental crowns.

Referring now to FIGS. 1 and 2, a basic embodiment of a novel tool for holding and manipulating cosmetic tooth veneers for use in dentistry is disclosed.

As shown in FIGS. 1 and 2, the dental veneer manipulating tool 30 includes an elongated cylindrical handle section 31, and a shorter elongated cylindrical tip support section 32 of smaller diameter joined coaxially to the handle section through a tapered diameter transition section 33.

While the dimensions of the tool 30 are for the most part not critical, handle section 31 should be of the proper dimensions to be easily manipulatable, in the manner of a pen or pencil. Thus, a length of approximately 5" and a diameter of about ¼" are suitable dimensions for handle section 31 of tool 30.

Tool 30 includes a relatively thin circular transverse cross section, outwardly concave tip 34 joined transversely to the outer end of the tip support section 32. The transverse perimeter outline of tip 34 must be smaller than the outline of ceramic dental veneers which the tip is used to contact. Since the approximate minimum dimensions of a veneer are about ¼" by ¼", a diameter of about ⅛" is a suitable diameter for tip 34. Hence, appropriate dimensions for tip support section 32 are approximately 1/16" diameter by about 1 to 1½ inches long.

Preferably, tool 30 is fabricated in a single piece from a plastic such as polypropylene, by injection molding, for example. Alternatively, the tool 30 can be made of other plastics, wood or metal, either as a one-piece assembly, or individual pieces fastened together to make a complete tool.

As shown in FIG. 1, the curvature of the concave tip section 34 is chosen to approximate the convex curvature of the outer or labial surface of a typical cosmetic tooth veneer A. FIG. 2 illustrates the relative proportions between the concave tip section 34 of tool 30, cosmetic tooth veneer A, an an upper right central incisor B which the veneer is to be laminated to.

The concave surface 35 of tip 34 is coated with a tacky adhesive layer 36. The adhesiveness of tacky adhesive layer 36 is sufficiently great that when the tip 34 is placed gently in contact with the outer convex surface of a cosmetic tooth veneer A, the veneer may be lifted and moved about while adhered to the tip.

In one embodiment of the adhesive dental veneer manipulating tool 30, the adhesive coating 36 is applied to tip 34 by the dental care professional just prior to using the tool. The adhesive coating may be applied by spraying the concave surface 35 of tip 34 with an aerosol-borne adhesive such as 3M Super 77 spray adhesive, manufactured by 3M Company, St. Paul Minn., and allowed to air-dry for about 30 to 60 seconds. Alternatively, the adhesive layer 36 may be applied to tip 34 by dipping the tip into a liquid adhesive such as 3M 77 Liquid Adhesive, or similar adhesives formulated for topical liquid application, and allowed to air-dry for about 30 to 60 seconds. Other, similar adhesives with greater or lesser adhesive properties may also be used. Drying time of the adhesive may be reduced by flowing air over the coated tip.

In another embodiment of the dental veneer manipulating tool 30, an adhesive coating 36 similar to the type used for temporarily cementing papers together and known as 3M Repositionable Adhesive is applied to the tip 34 of each tool during its manufacture. Other repositionable adhesive could also be used. The tip 34 of each tool is then protected by a patch 37 of smooth, glossy surface, non-adhering paper which may be easily peeled off of the tip just prior to using the tool, as shown in FIG. 3A. Non-adhering, silicone treated paper of the type used to hold self-adhesive labels, is a suitable material for patch 37.

FIG. 3B is a front end elevation view of a preferred tip shape in which the transverse cross-sectional shape of the tip is circular. FIGS. 3C and 3D illustrate tips 34A and 34B having alternate, square and rectangular transverse cross-sectional shapes, respectively, for tip 34. Other transverse cross-sectional shapes for tip 34 are utilizable in tool 30, in addition to the square and triangular shapes shown in FIGS. 3C and 3D, respectively. Preferably, each tip will have a slight concavity so as to more readily conform to the outer surface of a ceramic tooth veneer, and thereby facilitating the adhesion between the adhesive coating of the tip and the surface of the veneer, with the application of a very modest pressure between the tip and the veneer. As shown in FIGS. 1 and 2, typical veneers A have a single predominate axis of curvature which is vertically oriented. Therefore, if the outer lateral edges of the tips 34A and 34B are bent outwards slightly around a vertical symmetry axis V-V, as shown in FIGS. 3C and 3D, the tips will conform more closely to the surface of a ceramic veneer, facilitating use of the tip to pick up and transport the veneers.

After the tip 34 of tool 30 has been adhered to a ceramic dental veneer A, and the veneer transported to a desired location, the tip can be disengaged from the veneer by applying a slight pulling force between the veneer and tip. Disengagement may be facilitated by bending the tip 34 with respect to the veneer A, so that in effect, the tip is peeled away from the veneer.

In using tool 30 to laminate a ceramic dental veneer A to a tooth B, as shown in FIG. 2, the dentist first adheres the tip 34 of the tool to the outer convex, or labial, surface of the veneer, as described above. The dentist then uses the tool 30 to position the veneer A precisely in the desired position on the labial surface of a tooth which has been prepared for the lamination process, the last step in that preparation being the application of a coat of light-sensitive adhesive to the outer, or labial surface of the tooth. Excess light-sensitive adhesive is next squeezed out between the contacting areas of the veneer A and tooth B by pushing gently down on the veneer with tool 30. Vibrating the tool slightly facilitates this action.

With excess light-sensitive adhesive removed, and the veneer A positioned in precise registration with the tooth B, the outer surface of the veneer is illuminated with a small aperture, intense light source. Formerly, the light irradiation step was performed by a dental assistant, while the dentist held the veneer in place with his fingers, reducing the surface area of the veneer which could be irradiated. By using the tool 30 according to the present invention, the dentist can both position and irradiate a veneer without requiring the assistance of another person.

Since the ceramic veneer A is very thin, it is possible to fabricate the veneer so that it is sufficiently opaque to prevent the underlying tooth from being visible, yet sufficiently transparent to allow light from a high intensity source to be transmitted through the veneer to the light-sensitive adhesive between the veneer and the tooth, thereby initiating the photo-chemical reaction which sets the adhesive.

The transverse cross-section of tip 34 is small relative to the cross-section of a typical ceramic tooth veneer, and smaller than the area of finger tips formerly used to hold a veneer in place during the light irradiation process. Therefore, the use of tool 30 to hold a veneer in place allows a substantially greater portion of the surface of the veneer to be irradiated, substantially enhancing the light curing of the adhesive. The amount of light transmitted to the photosensitive adhesive can be increased even more by constructing tip 34 from a material which has a relatively high light transmittance.

A second embodiment of a dental veneer manipulating tool is shown in FIG. 4. The tool 40 shown in FIG. 4 is substantially similar to the basic embodiment 30 shown in FIG. 1. Thus, tool 40 has an elongated cylindrical handle section 41, a shorter, narrower diameter elongated cylindrical tip support section 42, a tapered diameter transition section 43, and a concave tip section 44. However, in tool 40, the longitudinal axis of the tip support section 42 is colinear with the longitudinal axis of the handle section 41, rather than being inclined with respect to that axis as in tool 30. In most applications for the dental veneer tool according to the present invention, tools with angled heads such as tool 30 would be found preferable by health care professionals, since the angled head allows freer access to the patient's mouth.

A third embodiment of a dental veneer manipulating tool is shown in FIG. 5. The tool 50 shown in FIG. 5 is of two-piece construction, permitting the elongated cylindrical handle portion 51 to be made of a different material than the tip section 55 and tip 57. Thus, as shown in FIG. 5, the tool 50 has an elongated cylindrical handle section 51 having at its forward end a straight end piece 52 bent at a slight angle with respect to the rear, major portion of the handle section. The end piece 52 has a straight, blind cylindrical bore 53 extending inward from the outer transverse face 54 of the end piece. Bore 53 is substantially coaxially located with respect to cylindrical end section 52.

The tool 50 includes a tip section 55 having an elongated cylindrical shank 56 adapted to fit within the bore 53 of handle section 51. Joined to the outer transverse surface of shank 56 is an enlarged diameter, concave tip 57. Tip 57 is similar in structure and function to the tips discussed above in conjunction with FIGS. 1 through 4. Thus, tip 57 may be molded as part of tip section 55, or be made of a different material, such as a more resilient plastic or elastomeric material than the shank 56 of the tip section.

As with the previously discussed embodiments of the dental veneer manipulating tool discussed above, the entire tool 50 may be mass produced from low-cost plastic, making it cost effective to dispose of the entire tool after using it on a patient. Thus, the time and expense of having to sterilize the tool can be eliminated. Alternatively, the handle section 51 can be made of a durable, readily sterilizable material such as stainless steel, while the tip sections 55 may be made of low-cost plastic or similar materials, permitting just the tip section to be disposed of after use on a patient.

FIG. 6 illustrates an alternate second embodiment of a tip for use with any of the previously discussed dental veneer manipulating tools according to the present invention. The tip 60 shown in FIG. 6 has a generally cylindrical shank section 61 and a thin, flat disc section 62 joined transversely to the outer transverse end of the shank section. Disc section 62 may have circular, square or triangular cross-sectional shape, as shown in FIGS. 3B, 3C, and 2D, respectively, and is preferably concentrically located with respect to shank section 61. As with the tips shown in FIGS. 3B, 3C and 3D, disc section 62 may be flat or concave.

The disc section 62 of tip 60 is preferably fabricated from a flexible material such as rubber, paper, or plastic, and contains an adhesive coating 64 on its outer planar surface 63. The adhesive coating 64 has limited adhesion characteristics, but is sufficiently tacky to grip and hold a ceramic tooth veneer when the disc 62 is pressed lightly against the outer surface of the veneer. A suitable choice for adhesive layer 64 is 3M Super 77 adhesive. However, other similar adhesive with more or less adhesion could also be used. Preferably, a patch of smooth, glossy paper 65 is placed in contact with the adhesive coating 64 during the manufacture of the tip 60, the patch being peeled off when it is desired to use the tip. The surface of the glossy paper from which patch 65 is made has sufficiently low adhesion to the adhesive coating 64 to permit the patch to be easily peeled away from the coating, while leaving the coating intact.

The shank section 61 of tip 60 may also be made of stiff paper, or of any other suitable material such as wood, metal, or plastic. Also, shank section 61 may be tubular, having a central bore adapted to receive the tip support section of a tool handle, such as tip support section 32 of tool 30 shown in FIGS. 1 and 2 and described above.

FIGS. 7 and 8 illustrate a third embodiment of a tip for use with a dental veneer manipulating tool according to the present invention. As shown in FIGS. 7 and 8, the tip 70 includes a generally cylindrical shank section 71. Near the outer transverse edge of the shank section, four rectangular tabs 72 extend radially outwards from ninety-degree spaced apart locations on a common circle, forming a cruciform structure as shown in FIG. 8. As shown in FIG. 7, the tabs 72 extend forward as well as radially outward from the outer cylindrical wall 73 of shank section 71, making a small, acute angle with respect to the forward directed longitudinal axis of the shank section.

The cruciform tip 70 is preferably made of a resilient material such as somewhat stiff paper or plastic. In a slightly altered version of tip 70, shank section 71 is made from tubular stock similar to a plastic drinking straw, with the rectangular tabs 72 being formed by making 90-degree spaced slits longitudinally through the wall of the straw, the slits extending longitudinally inwards from the outer annular end wall of the straw.

A modification of tip 70 is shown in FIG. 8A. In the modified tip 70A shown in FIG. 8A three rectangular tabs 72A extend radially outwards from one-hundred-and-twenty degree spaced apart locations on a circumference of a cylindrical shank section 71A.

A variation of the dental appliance veneer holder tool according to the present invention is shown in FIGS. 8B, 8C, and 8D. The tip 70B shown in FIGS. 8B, 8C and 8D provides an effective means for placing dental restorations such as crowns, bridges, and the like in a patient's mouth in perfect alignment with adjacent teeth. The tip 70B shown in FIGS. 8B-8D is similar to the cruciform tip 70 shown in FIGS. 7 and 8 and described above. Thus, tip 70B has four rectangular tabs which extend radially outwards from ninety degree spaced apart locations on a common circle to form a cruciform structure. However, the rectangular tabs are of two different lengths; an upper and lower pair of tabs 72A and 72B of equal length longer than the upper and lower tabs. As shown in FIGS. 8B and 8C, tabs 72C and 72D of tip 70B are of greater length than tabs 72A and 72B to permit them to contact the surfaces of two or more teeth in a dental restoration. Thus, tip 70B provides a very effective means for manipulating and installing dental restorations having more than one tooth.

Figure 11:
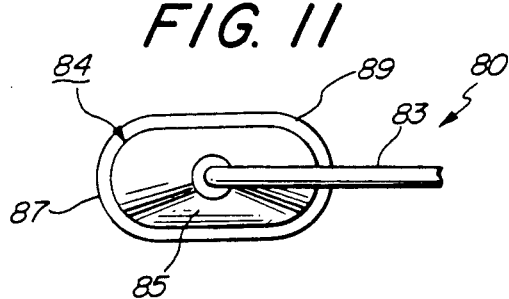
FIG. 11 is an upper plan view of the tool of FIG. 10.

Another embodiment of the dental restoration holder and placement tool according to the present invention is shown in FIGS. 10 and 11. The tool 80 shown in FIGS. 10 and 11 provides an effective means for placing a crown in a patient's mouth in perfect alignment with adjacent teeth. Moreover, the tool 80 may serve as a highly effective seating fixture or bite plate to facilitate cementing the crown in place after placement in a patient's mouth, as will be described below.

Referring now to FIGS. 10 and 11, the resilient crown manipulating tool 80 according to the present invention is seen to comprise an elongated cylindrical handle section 81 having a shorter, smaller diameter elongated extension section 82 having an end 83 angled with respect to the common longitudinal axis of the handle section and extension section.

The tip 84 of tool 80 is a generally lenticular-shaped body having a convex upper surface 85, a generally flat lower surface 86, and a generally oval plan view outline 87. The tip 84 is molded from a semi-soft plastic or elastomeric material. Preferably, the tip 84 is made from a semi-soft resilient compound selected from the group comprising plasticized polyvinyl chloride (PVC) known as "PLASTISOL" in the trade, plasticized vinyl, plasticized polyurethane or thermoplastic elastomer (plastic rubber base material). A preferred hardness for the finished tip 84 would be in the range of 20 to 95 on the Shore hardness A scale.

As shown in FIG. 10 the bottom surface 86 of tip 84 is coated with a tacky adhesive surface 88 of the type discussed previously for the basic embodiments of the dental restoration holder and placement tool. The adhesive surface 88 may be formed on the bottom surface 86 of tip 84 by spraying or dipping just prior to use of the tip. Alternatively, the coating may be applied during the manufacture of tip 84. When pre-applied during the manufacturing process, a patch 89 of smooth non-sticky paper such as silicone treated paper is preferably adhered to surface 88 until tool 80 is to be used.

As may be seen best by referring to FIG. 11, tip 84 of tool 80 is provided with a blind bore 90 adapted to insertably receive the end 83 of handle section 81 of the tool. Bore 90 extends inwards at an angle from a side of the upper convex surface 85 of tip 84. The diameter of bore 90 is of the proper size to snugly hold end 83 of handle section 81, yet permit its withdrawal with a small pulling force, for a purpose described below.

In an alternate method of removably attaching end 83 of handle section 81 to tip 84, end 83 is sharpened and inserted directly into the desired position in the tip, the resilience of the tip material causing the handle end to be held by the tip.

The crown installation tool 80 is used to pick up and place a dental crown casting by first removing the protective sheet 89 from the tacky surface 88 of the tip 84. The tacky surface 88 of the tip 84 is then pressed down onto the biting surface of the crown. The plasticity of the material from which the tip 84 is made permits the tip to deform from its original lenticular shape to a shape conforming to the irregular biting surface of the crown. This ensures good adhesive contact between the tacky surface 88 of the tip 84 and the irregular surface of the crown.

After the tip 84 of tool 80 has been adhered to a crown as described above, the tool is used to transport the crown to the mouth of the patient, and manipulate the crown into precise placement on a tooth structure which has been prepared and coated with a bonding material. The patient may then bite down onto the upper convex surface 85 of tip 84, pressing the crown firmly down on the prepared tooth structure. At this time, the handle section 81 may be withdrawn from the tip 84 of the tool, allowing the patient to comfortably hold the crown tightly in place while the bonding agent cures. Typically, this takes five to ten minutes, or a little longer. After curing has taken place, the dentist removes the tip 84 and discards it. Thus, the tool 80 provides a highly effective and economical seating fixture or biting plate for the installation of crowns, as well as a highly effective holder and placement tool for manipulating the crown.

Figure 12:
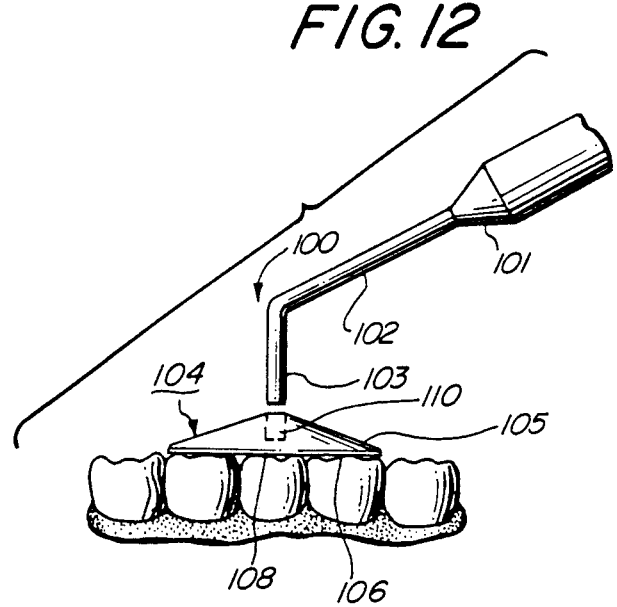
FIG. 12 is a front elevation view of a variation of the tool of FIG. 10 which is adapted to installing dental bridges.
Figure 13:
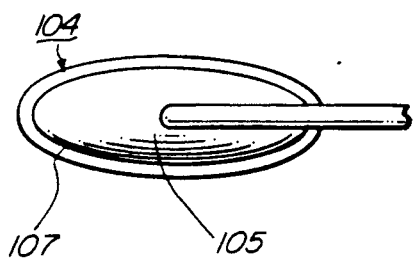
FIG. 13 is an upper plan view of the tool of FIG. 12.

FIGS. 12 and 13 illustrate a modification of the resilient crown manipulating tool 80 shown in FIGS. 10 and 11.

The tool 100 shown in FIGS. 12 and 13 is particularly well adapted to use as a manipulating and placement tool, and bite plate or seating plate, for the installation of bridges comprising two or more replacement teeth castings. The bridge holding tool 100, shown in FIGS. 10 and 11, is substantially identical in overall structure and function to the crown installation tool 80 described above. However, the tip 104 of tool 100 is longitudinally elongated to adapt the tip to adhesively contact the biting surfaces of two replacement teeth castings at opposite ends of a bridge.

A container for transporting and dispensing a quantity of dental veneer manipulating tools of the type described above is shown in FIG. 9.

The container 80 shown in FIG. 9 includes a box 81 having a rectangular base 82 and four side walls disposed perpendicularly upwards from the base, of relatively small height. Thus, box 81 has a substantially elongated rectangular lower side wall 83, and an identically shaped upper side wall 84 parallel to the lower side wall. A slightly elongated rectangular left side wall 85 perpendicularly joins the left sides of lower and upper side walls 83 and 84, while an identically shaped right side wall 86 parallel to the left side wall perpendicularly joins the right sides of the upper and lower side walls.

The upper side wall 84 of box 81 contains a plurality of identical circular holes 87 through the thickness dimension of the side wall, spaced at regular longitudinal intervals. The diameter of holes 87 is of the appropriate size to snugly receive the outer cylindrical surface of cylindrical handle 31 of a tool 30.

Extending upwards from the base 82 of box 81 is a plurality of identical rectangular lugs or spacing partitions 88, spaced at regular longitudinal intervals, but in staggered vertical relationship to holes 87. The relative size and spacing between adjacent pairs of partitions 88 are appropriate to hold the narrower forward portion of each tool 30 inserted through a hole 87 in snug confinement, with the longitudinal axis of each tool 30 disposed perpendicularly to the lower side wall 83 of box 81. Thus positioned, the outer transverse surface of the tip 34 of each tool 30 is parallel to the inner, upper surface 89 of lower side wall 83. A single strip of smooth, non-sticky protective paper 90 is contained on the upper surface 89 of lower side wall 83, and each tip pressed gently in adherence against the protective paper.

The container 80 may be made of cardboard, plastic or any other suitable sterilizable and disposable material. Partitions 88 may be made of a single strip of plastic or cardboard formed into a continuous corrugated structure of the type depicted in FIG. 9. A cover of any suitable type is included with container 80 to form an air-tight enclosure for the tools 30, guaranteeing their sterility. Plastic film shrink-wrapped around the container 80 and handles 31 of tools 30 could be used for this purpose.

To dispense dental veneer manipulating tools 30 from container 80, the dentist would first break the protective cover enclosing container 80, and then pull a tool 30 out from box 80 by grasping its handle 31 and pulling the handle away from the lower side wall surface 89 of the box, away from the protective paper 90 protecting the adhesive coating on the tip 34 of the tool. Thus, the container 80 provides a convenient means of supplying and dispensing a quantity of sterile, disposable ceramic dental veneer manipulating tools 30 according to the present invention.

It should be evident, of course, that the tip 34 of each tool 30 could be provided with an individual protective patch 37, rather than the common protective paper strip 90, with the individual protective patch being peeled off of the tip after the tool has been withdrawn from the container 80.

What is claimed is:

1. A device for manipulating thin fragile objects such as ceramic tooth veneers comprising:
   (a) an elongated pencil-like handle structure, and
   (b) a tip fastened to one end of said handle structure said tip comprising:
      (i) a generally cylindrical shank section adapted to fasten to an outer transverse end of said handle structure, and
      (ii) a plurality of thin, generally uniform thickness tabs flexibly attached to said shank section, said tabs extending outwards from circumferentially spaced apart locations around the outer cylindrical surface of said shank section, at least two of said tabs being non-colinear with each other, the outer surface of said tabs having thereon an adhesive coating adapted to releasably attach to a surface of said object to be manipulated.

2. The device of claim 1 wherein said plurality of tabs is further defined as comprising four polygonal cross-section appendages spaced apart at 90-degree circumferential locations to form in transverse cross-sectional view a cruciform structure.

3. The device of claim 2 wherein at least one of said appendages is of different radial extent than the other appendages.

4. The device of claim 1 wherein said plurality of tabs is further defined as comprising three polygonal cross-section appendages spaced apart at 120 degree circumferential locations.

* * * * *